US00PP33541P2

(12) United States Plant Patent
Carruth

(10) Patent No.: US PP33,541 P2
(45) Date of Patent: Oct. 12, 2021

(54) CLIMBING ROSE PLANT NAMED 'WEKAUSUJUCTON'

(50) Latin Name: *Rosa hybrida*
Varietal Denomination: WEKausujucton

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 16/949,947

(22) Filed: Nov. 20, 2020

(51) Int. Cl.
*A01H 5/02* (2018.01)
*A01H 6/74* (2018.01)

(52) U.S. Cl.
USPC ..... Plt./112

(58) Field of Classification Search
USPC ..... Plt./111–113, 134–135, 145–146
CPC ..... A01H 5/02; A01H 5/00; A01H 5/0222; A01H 6/74; A01H 6/749
See application file for complete search history.

(56) References Cited

U.S. PATENT DOCUMENTS

PP17,126 P2 10/2006 Warner

OTHER PUBLICATIONS

Edmunds' Roses, retrieved on Mar. 23, 2021, retrieved from the Internet at https://www.edmundsroses.com/product/E25444/6, 4 pp. (Year: 2021).*
Otto & Sons Nursery Rose List 2020, retrieved on Mar. 23, 2021, retrieved from the Internet at https://ottoandsonsnursery.com/wp-content/uploads/2020/10/Otto.Rose_.Availability.10.14.20.pdf, 6 pp. (Year: 2020).*
"MACamster' Rose Description", https://www.helpmefind.com/rose/pl.php?n=41944, McGredy Roses International (New Zealand), 1 page, accessed Jan. 28, 2021.

* cited by examiner

*Primary Examiner* — June Hwu
(74) *Attorney, Agent, or Firm* — McKee, Voorhees & Sease, PLC

(57) ABSTRACT

A new variety of Climbing rose suitable for garden decoration, having flowers of gold coloration.

1 Drawing Sheet

Classification: The present invention relates to a new *Rosa hybrida* plant.

Variety denomination: The new plant has the varietal denomination 'WEKausujucton'.

BACKGROUND OF THE INVENTION

This invention relates to a new and distinct variety of Climbing Rose. It has a non-disseminated seedling of my creation as its seed parent with the following genetic origin Autumn Sunset x Julia Child and as its pollen parent the variety known as 'MACamster' (not patented).

SUMMARY OF THE INVENTION

Among the features which distinguish the new variety from other presently available and commercial rose cultivars known to the inventor are the following combinations of characteristics: its elegant gold flowers, its excellent color stability throughout the life of the flower, its vigorous growth and its abundant blooms. The plant has a spreading climbing growing habit, suitable for outdoor garden decoration.

Asexual reproduction of the new variety by budding as performed in Wasco, Calif., shows that the foregoing and other distinguishing characteristics come true to form and are established and transmitted through succeeding asexual propagations. 'WEKausujucton' may be asexually propagated by cuttings, budding and grafting. The budding and grafting successfully occurred on the plant/rootstock *Rosa hybrida*. 'Dr. Huey' (not patented).

COMPARISON WITH PARENTS

The new rose may be distinguished from its seed parent, a non-disseminated seedling of my creation by the following combination of characteristics: whereas 'WEKausujucton' bears double flowers (about 32 to 47 petals) of gold coloration, the non-disseminated seedling bears double flowers of brilliant orange coloration with significantly lesser petalage (about 18 to 24 petals). The new variety bears medium to somewhat large sized flowers (about 8.3 to about 11.1 cm. in diameter), whereas the seed parent bears smaller flowers (about 7.0 to about 8.5 cm. in diameter).

The new variety may be distinguished from its pollen parent, 'MACamster' by the following combination of characteristics: whereas 'WEKausujucton' bears double flowers (about 32 to 47 petals) of gold coloration, 'MACamster' bears double flowers of golden apricot coloration with lesser petalage (about 26 to 40 petals). The new variety is classified as a Climbing rose with a spreading climbing tall growing habit with canes about 250 cm. to about 300 cm. in length, whereas the pollen parent classified as a Floribunda rose with an upright significantly shorter growing habit (about 90 to about 140 cm. in height).

COMPARISON WITH THE CLOSEST COMMERCIALLY AVAILABLE CULTIVAR

The new variety may be distinguished from its closest commercially available cultivar, 'CHEwgoldtop' (U.S. Plant Pat. No. 17,126) by the following combination of characteristics: whereas 'WEKausujucton' bears double flowers (about 32 to 47 petals) of gold coloration, 'CHEwgoldtop' bears double flowers of yellow coloration with significantly lesser petalage (about 25 petals). The flowers of the new variety have a moderate fruity to tea fragrance, whereas the flowers of the closest commercially available cultivar have a moderate spicy fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of November. Phenotypic expression may vary with environmental, cultural and climatic conditions, as well as differences in conditions of light and soil.

Flower: The new variety sometimes bears its flowers singly, sometimes in clusters of three to five or more per stem. Flowers may be borne in regular rounded clusters on strong medium to long length stems (about 26 to about 150 cm.). The cluster ranges from about 17.0 to about 19.5 cm. in diameter. Outdoors, the plant blooms abundantly and nearly continuously during the growing season. The flowers have a moderate fruity to tea fragrance.

Bud: The peduncle is about 1.7 to about 7.3 cm. in length, of average to somewhat heavy caliper (about 0.2 to about 0.4 cm. in diameter), and usually erect. It is usually smooth, with few hairs. Peduncle color is between 146C and 148A often moderately suffused, especially on the side exposed to the sun, with between 187B and 187A. Before the calyx breaks, the bud is about 1.4 to about 2.3 cm. in diameter at the widest point, about 1.6 to about 2.3 cm. in length, and moderately ovoid to somewhat pointed in shape. The surface of the bud bears between 6 to 9 foliaceous appendages with some hairs, usually with slender entire foliaceous parts extending beyond the tip of the bud about ½ or more of its length. Bud color is between 137C and 147B sometimes lightly suffused, especially on the side exposed to the sun, with between 187B and 187A. The sepals are 5 per flower, about 2.3 to about 3.7 cm. in length and about 0.8 to about 1.3 cm. in width at the widest point. The outer surface color of the sepal is between 137C and 147B sometimes lightly suffused, especially on the side exposed to the sun, with between 187B and 187A. The outer surface of the sepal is smooth and bears between 0 to 4 foliaceous appendages with some hairs. The inner surface color of the sepal is near 146B broadly bordered by near 137A. After the sepals open, the inner surface color is often lightly suffused, especially on the area exposed to the sun, with between 187B and 187A. The inner surface of the sepal is covered with fine wooly tomentum; sepal margins are entire and lined with few stipitate glands and some hairs. The sepals are fugacious, and usually straight in shape with acute apices. The receptacle of the flower is of medium length (about 0.4 to about 0.7 cm.) and average in caliper (about 0.8 to about 1.4 cm. in diameter). The receptacle is urn-shaped in form. Its surface is smooth with very few hairs and with somewhat thin fleshy walls. The receptacle color is between 144A and 147B. As the petals open (after the calyx breaks), the bud is about 2.1 to about 3.4 cm. in diameter at the widest point, about 2.3 to about 4.4 cm. in length, and ovoid to somewhat pointed in form. The color of the under surfaces of the newly opened petals is between 24B and 26B sometimes lightly suffused with between 53B and 53C. At the point where the petal attaches, there is a somewhat large zone of between 2B and 3B. The color of the upper surfaces of the newly opened petals is between 22A and 24B. At the point where the petal attaches, there is a somewhat large zone of between 6A and 7A.

Bloom: When fully open, the bloom ranges from about 8.3 to about 11.1 cm. in diameter. Petalage is double with about 32 to 47 petals and about 3 to 14 petaloids irregularly arranged. When partially open, the bloom form is moderately high centered to somewhat cupped, and the petals are moderately tightly spiraled to somewhat cupped with petal edges moderately reflexed outward. When fully open, the bloom form is more cupped, and the petals are loosely cupped to somewhat undulated with petal edges moderately reflexed outward.

Petals: The substance of the petals is moderately heavy and of medium to somewhat thick thickness, with upper surfaces slightly satiny and under surfaces moderately shiny. The petals are about 3.8 to about 5.7 cm. in length and about 2.8 to about 5.4 cm. in width at the widest point. Petal margins are entire. The outer petals are broadly rounded to somewhat obovate in shape with rounded apices. The inner petals are moderately obovate in shape with rounded apices and sometimes slightly notched with one notch. Petaloids are about 1.4 to about 5.1 cm. in length and about 0.6 to about 3.5 cm. in width at the widest point. Petaloids are irregularly shaped moderately obovate to oblanceolate to somewhat subulate with rounded apices.

Newly opened flower: The under surface color of the outer petals is between 19B and 22B sometimes lightly suffused with between 53C and 53D. There is no visible change in coloration at the point where the petal attaches. The upper surface color of the outer petals is between 24D and 20D. At the point where the petal attaches, there is a large zone of between 7D and 5C. The under surface color of the intermediate and inner petals is between 19B and 22B. The upper surface color of the intermediate and inner petals is between 19B and 20D. The under and upper surface colors of the petaloids are similar in coloration to the upper and under surfaces of the intermediate and inner petals. The general tonality of the newly opened flower is between 19B and 20D.

Three-day-old flower: The under surface color of the outer petals is between 20D and 27A. At the point where the petal attaches, there is a large zone of between 6D and 5D. The upper surface color of the outer petals is between 23D and 27A. At the point where the petal attaches, there is a large zone of between 3C and 4B. The under and upper surface color of the intermediate and inner petals is between 18C and 27A. The under and upper surface colors of the petaloids are similar in coloration to the upper and under surfaces of the intermediate and inner petals. The general tonality of the three-day-old flower is between 18C and 27A. On the spent bloom, the petals usually drop off cleanly. In November in Wasco, Calif., blooms on the bush growing outdoors generally last about four to five days. Cut roses from plants grown outdoors and kept at normal indoor living temperatures generally last about four to five days.

Male reproductive organs: Stamens are many in number (average about 230) and are arranged regularly about the pistils; a few are mixed with petaloids. The filaments are of moderately short to somewhat long length (about 0.5 to about 1.7 cm.) most with anthers. Filaments are between 5A and 7A in color often lightly suffused with between 53B and 53C. The anthers are of medium size for the class and all open approximately at the same time. Anther color when immature is near 20A on the external part and near 13D on the internal part. Anther color at maturity is near 164A on the external part and near 200A on the internal part. Pollen is moderate and between 19C and 18C in color.

Female reproductive organs: Pistils vary in number (average about 130). The styles are moderately even, somewhat short to average in length (about 0.4 to about 0.8 cm.), average in caliper, and loosely bunched. Stigma color is near 14D. Style color is between 154D and 1D often heavily suffused with between 60A and 60B. Ovaries are usually all enclosed in the calyx. The ovaries are of small size and between 158B and 158C in color. Hips are of somewhat short to average length (about 1.2 to about 1.7 cm.), rounded in form with a flat top and base, and between 28A and 30B in color when ripe. The hip surface is smooth with thick fleshy walls. The seeds are irregularly rounded, smooth in texture, approximately 18 to about 29 per hip, about 0.4 to about 0.5 cm. in diameter at the widest point and between 165C and 164B in color.

Foliage: The compound leaves are usually comprised of three to seven leaflets and are borne abundantly. The five-leaflet leaves are about 8.0 to about 15.7 cm. in length and about 6.8 to about 11.7 cm. in width at the widest point, moderately leathery to somewhat crisp in texture on both sides, and with a strong glossy finish on the upper side and a weak to medium glossy finish on the under side. The leaflet margin undulation is absent. The leaves have a pinnate venation pattern. The terminal leaflets are about 4.0 to about 8.6 cm. in length and about 2.2 to about 4.8 cm. in width at the widest point, shaped moderately oval to somewhat ovate with acute to somewhat acuminate apices and rounded to somewhat acute bases. Their margins are usually simply serrate. The upper surface color of the mature leaf is between 137A and 147A. The under surface color of the mature leaf is between 146B and 147B. The under and upper colors of the leaf veins on the mature leaf are similar in coloration to the upper and under surfaces colors of the mature leaf. The upper surface color of the young leaf is between 137C and 146B, often moderately suffused with between 187B and 187A. The under surface color of the young leaf is between 146B and 148A, often moderately suffused with between 187B and 187A. The under and upper colors of the leaf veins on the young leaf are similar in coloration to the upper and under surfaces colors of the young leaf. The rachis is about 4.2 to about 8.4 cm. in length, about 0.1 to about 0.2 cm in width at the widest point, and rough. The upper side is deeply grooved with some hairs and few stipitate glands on the edges of the grooves. The under side of the rachis is rough with few small prickles. The rachis color is near 146C on the under side and near 146B on the upper side, often heavily suffused on the young leaves with between 187B and 187A. The stipules are about 1.3 to about 2.4 cm. in length and medium to somewhat wide (about 0.4 to about 0.7 cm.) with moderately long straight points that usually turn out at an angle of more than 45 degrees and sometimes recurve toward the stem. The under and upper surface color of the stipule is near 137C. The upper and under surfaces of the stipules are smooth in texture. The petiole is somewhat light in caliper and rough. The upper side is deeply grooved with some hairs and few stipitate glands on the edges of the grooves. The under side of the petiole is rough with few small prickles. The petiole is about 0.5 to about 2.2 cm. in length and about 0.1 to about 0.2 cm at the widest point. The petiole color is near 146C on the under side and near 146B on the upper side, often heavily suffused on the young leaves with between 187B and 187A. The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Wasco, Calif. The plant's winter hardiness and drought/heat tolerance are yet to be determined.

Growth: The plant has a spreading climbing tall growing habit with canes about 250 cm. to about 300 cm. in length with full branching. It displays vigorous growth and the canes are somewhat light in caliper for the class (about 1.4 to about 2.1 cm. in diameter at the widest point). The color of the major stems is between 146B and 147B. The major stems are rough in texture and they bear some large prickles that are about 0.8 to about 1.3 cm. in length. The large prickles are angled slightly downward with a moderately short somewhat narrow oval base; prickle color is between 165B and 164A often moderately suffused with between 201B and 201C. The major stem bears few small prickles of similar shape and coloration. The color of the branches is between 146B and 146A. The branches are rough in texture and they bear some large prickles which are of similar size and shape to the large prickles on the major stems; prickle color is between 161A and 162A. The branches bear very few small prickles of similar shape and coloration. The color of the new shoots is between 146C and 146B often heavily suffused with between 187B and 187C. The new shoots are rough in texture and they bear some large prickles which are of similar size and shape to the large prickles on the major stems; prickle color is between 146C and 146D usually heavily suffused with between 187B and 187C. The shoots bear few small prickles of similar shape and coloration.

I claim:

1. A new and distinct variety of Climbing rose plant designated 'WEKausujucton', substantially as described and illustrated herein.

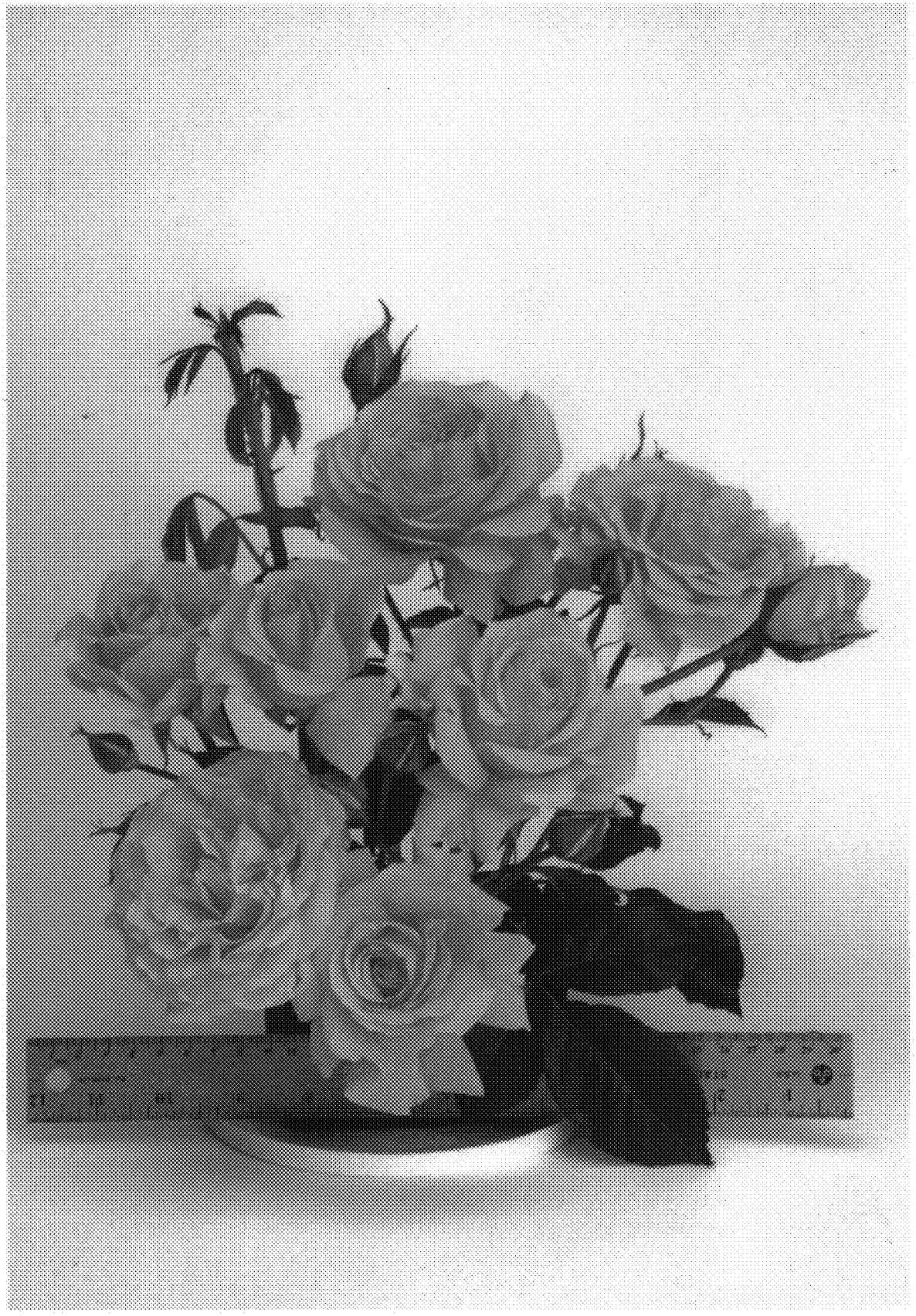

* * * * *